United States Patent [19]

Komiyama et al.

[11] Patent Number: 4,701,324

[45] Date of Patent: Oct. 20, 1987

[54] NOVEL CELL-CIDAL ANTIBIOTIC 82-85-8A AND ITS PRODUCTION

[75] Inventors: Kanki Komiyama; Shinji Funayama, both of Yokohama; Iwao Umezawa, Tokyo, all of Japan

[73] Assignee: The Kitasato Institute, Tokyo, Japan

[21] Appl. No.: 799,724

[22] Filed: Nov. 18, 1985

[30] Foreign Application Priority Data

Mar. 27, 1985 [JP] Japan .................................. 60-60833

[51] Int. Cl.[4] .......................... A61K 35/74; C12P 1/06
[52] U.S. Cl. ..................................... 424/118; 435/169
[58] Field of Search .......................... 424/118; 435/169

*Primary Examiner*—Jerome D. Goldberg
*Attorney, Agent, or Firm*—Young & Thompson

[57] ABSTRACT

Antibiotic 82-85-8A, or a pharmacologically acceptable non-toxic salt thereof, having the following physico-chemical properties:

(1) Elementary analysis: $C_{31}H_{47}N_8O_{10}Cl$ (determined by high resolution mass spectrometry)
(2) Molecular weight: 726.5 (determined by field desorption mass spectrometry and calculated from elementary analysis)
(3) Melting point: 162°–167° C. (partially immersed at 160° C., completely melted at 167° C., no browning)
(4) Specific rotation: $[\alpha]_D^{20} = -56°$ (c=0.24, methanol)
(5) Ultraviolet absorption spectrum (in methanol): shown in FIG. 1
(6) Infrared absorption spectrum (KBr): shown in FIG. 2
(7) Solubility:
   soluble: chloroform, dichloromethane, ethyl acetate, methanol, ethanol,
   slightly soluble: acetone,
   insoluble: hexane, water;
(8) Color reaction:
   Positive: iodine, sulfuric acid, Dragendorf reaction
   Negative: ninhydrin, ferric chloride
(9) Nature: weakly basic substance.

The antibiotic is produced by culturing an antibiotic-82-85-8A-producing microorganism belonging to genus Streptomyces, for example Streptomyces sp. No. 82-85, FERM-P No. 8140.

3 Claims, 3 Drawing Figures

NOVEL CELL-CIDAL ANTIBIOTIC 82-85-8A AND ITS PRODUCTION

This invention relates to a novel antibiotic 82-85-8A having antimicrobial and cell-cidal activity, and its production.

Prior known peptide lactone series antibiotics produced by genus Streptomyces are monamycin-$G_1$, -$G_2$, -$H_1$, -$H_2$ and -I [J. Chem. Soc. (c), 526–537 (1971)].

We have found that a species of Streptomyces isolated from a soil sample obtained in Kanagawa-ken, Japan produces an antibiotic substance having strong antibacterial activity against Gram positive bacteria and growth inhibitory activity against HeLa $S_3$ cells. The active substance has been isolated from the cultured broth and purified to determine its physico-chemical properties as hereinbelow illustrated. A substance having such physico-chemical properties has never been known among prior antibiotic substances and hence it was designated as 82-85-8A.

An object of the present invention is accordingly to provide a novel antibiotic 82-85-8A or its pharmacologically acceptable non-toxic salt.

Another object of the present invention is to provide a process for the production of antibiotic 82-85-8A which comprises culturing an antibiotic-82-85-8A-producing microorganism belonging to genus Streptomyces, accumulating antibiotic 82-85-8A in a cultured broth and isolating the thus-produced antibiotic 82-85-8A therefrom, and if required changing it to a pharmacologically acceptable non-toxic salt thereof.

Antibiotic-82-85-8A-producing microorganisms belong to the genus Streptomyces, and the Streptomyces strain 82–85 isolated by the present inventors is illustrative only.

The taxonomical properties of the said strain are illustrated hereinbelow:

A. Morphology

An observation of Waksman agar plate medium at 27° C. for 14 days culture of a strain 82-85 is as follows:

Hyphal growth. Substrate mycelia are not split. Aerial mycelia are irregularly branched and not whirly branching. No sporangia are observed on the top of aerial mycelia. Straight spore chains are linked with over 20 spores. The spore form is elliptical to cylindrical with smooth surfaces of 0.9–1.4 μm on the minor axis.

B. Growth Conditions on Various Media

Growth conditions on various media at 27° C. for 14 day's culture are illustrated as follows:

| Medium | Growth | Reverse Side | Aerial Mycelia | Soluble Pigment |
|---|---|---|---|---|
| Yeast-maltose agar (ISP medium 2) | Medium | Pinkish white | Pale orange | Ocher |
| Oatmeal agar (ISP medium 3) | Good | Pale brown | Pale orange | Ocher |
| Starch-inorganic agar (ISP medium 4) | Good | Pale orange | Pale orange | Light ocher |
| Glycerol-asparanine agar (ISP medium 5) | Good | Light yellow | White | Light yellow |
| Peptone-yeast-iron agar (ISP medium 6) | | Yellowish brown | Gray | Light brown |
| Tyrosine agar (ISP medium 7) | Good | Dark brown | Pale yellow | Brown |

C. Physiological Properties

1. Growth temperature: 20°–37° C., optimum growth temperature: approx. 27° C.
2. Liquefaction of gelatine (glucose-peptone-gelatine medium): negative
3. Hydrolysis of starch (starch-inorganic salt agar medium): positive
4. Coagulation of skim-milk and peptonization (10% skim-milk medium): negative
5. Formation of melanine pigment (peptone-yeast-iron agar medium and tyrosine agar medium): negative
6. Formation of $H_2S$ (peptone-yeast-iron agar medium): negative
7. Tyrosinase reaction (tyrosine agar): negative

D. Utilization of Carbon Sources

Assimilation of carbon sources was observed on Pridham-Gottlieb agar medium at 27° C. for 1-2 months.

| | |
|---|---|
| L—arabinose | + |
| D—xylose | + |
| D—mannitol | + |
| L—rhamnose | + |
| sucrose | + |
| inositol | + |
| D—fructose | + |
| raffinose | − |

E. Composition of Cell Wall

According to analysis by the method of Becker et al. [Appl. Microbiol., 13, 236-243 (1965)], LL-type diaminopimelic acid was detected.

Referring to the above taxonomical properties, the strain 82-85 belongs to genus Streptomyces, and the strain has been deposited in The Fermentation Research Institute as FERM-P No. 8140.

In general, Streptomyces is easy to mutate and a mutant strain can be obtained by natural or artificial mutation techniques such as ultraviolet or X-ray irradiation or by means of treating with a mutagenic agent using N-methyl-N'-nitro-N-nitrosoguanidine and ethyl methanesulfonate. These artificial or natural mutants or the strain 82–85 belonging to genus Streptomyces which can produce antibiotic 82-85-8A are included for use in the present invention.

In the present invention, a strain belonging to genus Streptomyces which can produce antibiotic 82-85-8A, is cultured in a suitable medium. Any conventional culture medium for Streptomyces can be used. The medium to be used is a nutrient medium containing assimilable carbon sources, digestible nitrogen sources and, if required, inorganic salts. Examples of assimilable carbon sources are glucose, molasses, starch, dextrin, glycerin or organic acids. Digestible nitrogen sources are, for example, organic nitrogen sources such as peptones, meat extracts, yeast extracts, dry yeast, soybean powder, corn steep liquor, cotton seed cake, casein, soybean protein hydrolyzate, amino acids or urea, and inorganic nitrogen sources such as nitrates or ammonia. Inorganic salts such as sodium salts, potassium salts, calcium salts or magnesium salts are added if required. Other trace nutrients, growth factors or precursors of the antibiotic 82-85-8A can also be added to the medium.

Conventional culture is aeration culture with shaking or submerged culture. Under industrial conditions, submerged aeration culture is preferable. The pH of the culture medium is preferably neutral and the culturing temperature is generally 24°–30° C., preferably at 27° C. The culturing time in a liquid medium is generally 3–6 days for optimum antibiotic accumulation. When the amount of antibiotic reaches a maximum in a culture medium, the culture is preferably terminated. Culturing conditions such as the composition of culture medium, temperature, agitation speed, and aeration rate can be controlled according to such conditions as the strain involved, etc. Anti-foaming agents such as silicone oils, vegetable oils or surface-active agents can also be added.

The thus-produced antibiotic 82-85-8A mainly accumulates in the culture filtrate, and so the cultured medium is filtered after adding a filter aid such as Celite (trade name) or Hyfrosuper-cell (trade name), or is centrifuged to separate mycelia from the cultured filtrate.

Isolation of antibiotic 82-85-8A can be effected by making use of the fact that the antibiotic is insoluble in hexane and water, and is soluble in a lower alcohol such as methanol or ethanol, or chloroform, dichloromethane or butyl acetate, and is weakly basic.

Antibiotic 82-85-8A can be extracted from the cultured filtrate with a water-immiscible organic solvent such as chloroform, dichloromethane or butyl acetate. The organic layer is washed, if required, with dilute ethylene diamine tetraacetate solution for removal of metallic ions and is dehydrated by adding a dehydration reagent such as anhydrous sodium sulfate or anhydrous magnesium sulfate. The dehydrated organic layer is concentrated to remove the organic solvent. In order to avoid decomposition of the antibiotic 82-85-8A, the temperature during concentration should be preferably below 60° C. An organic solvent such as hexane or petroleum ether is added to the concentrated residue to precipitate the antibiotic. The precipitate is washed several times with hexane and filtered or centrifuged to obtain crude brown-colored antibiotic 82-85-8A.

Further purification can be effected by various operations such as the difference in solubility of a contaminant and the antibiotic, the difference in partition of two immiscible liquid layers, or the difference in adsorption on an adsorbent carrier, in which latter case a chromatographic operation is preferable.

Examples of chromatography are adsorption chromatography using an adsorption resin such as silica gel, alumina, active carbon or HP-20 resin (trade name), reverse phase partition chromatography using silylated silica gel or octadecyl silylated silica gel, gel-filtration chromatography using Sephadex LH-20 or Toyopearl (trade name), or ion-exchange chromatography using DEAE-cellulose, DEAE-Sephadex or DEAE-Toyopearl (trade names).

Antibiotic 82-85-8A can be purified by combining or repeating the chromatography, electrophoresis, counter current exchange, ultra-filtration or distillation. For example, crude antibiotic dissolved in a small amount of chloroform or benzene is adsorbed on a previously packed silica-gel column and eluted with a mixed solution of chloroform-methanol; then the combined active fractions are concentrated in vacuo. The thus-obtained active substance dissolved in a small amount of methanol is charged on a reverse phase silica-gel column and eluted with a mixed solution of methanol-water to purify antibiotic 82-85-8A.

Antibiotic 82-85-8A is a weakly basic substance and is prepared as a salt. The salt is a pharmacologically acceptable non-toxic salt, for example an acid addition salt such as an inorganic salt like the hydrochloride, sulfate, phosphate or carbonate or an organic salt like the acetate, propionate, tartrate, citrate, malate, glutamate, aspartate, methanesulfonate or p-toluene sulfonate. Other known pharmacologically acceptable acid addition salts can be prepared.

The physico-chemical properties of antibiotic 82-85-8A are illustrated as follows:

(1) Elementary analysis: $C_{31}H_{47}N_8O_{10}Cl$ (high resolution mass spectrometry)

(2) Molecular weight: 726.5 (field desorption (FD) mass spectrometry and calculated from elementary analysis)

(3) Melting point: 162°–167° C. (partially immersed at 160° C., completely melted at 167° C., no browning)

(4) Specific rotation: $[\alpha]_D^{20} = -56°$ (c=0.24, methanol)

Figure 1:
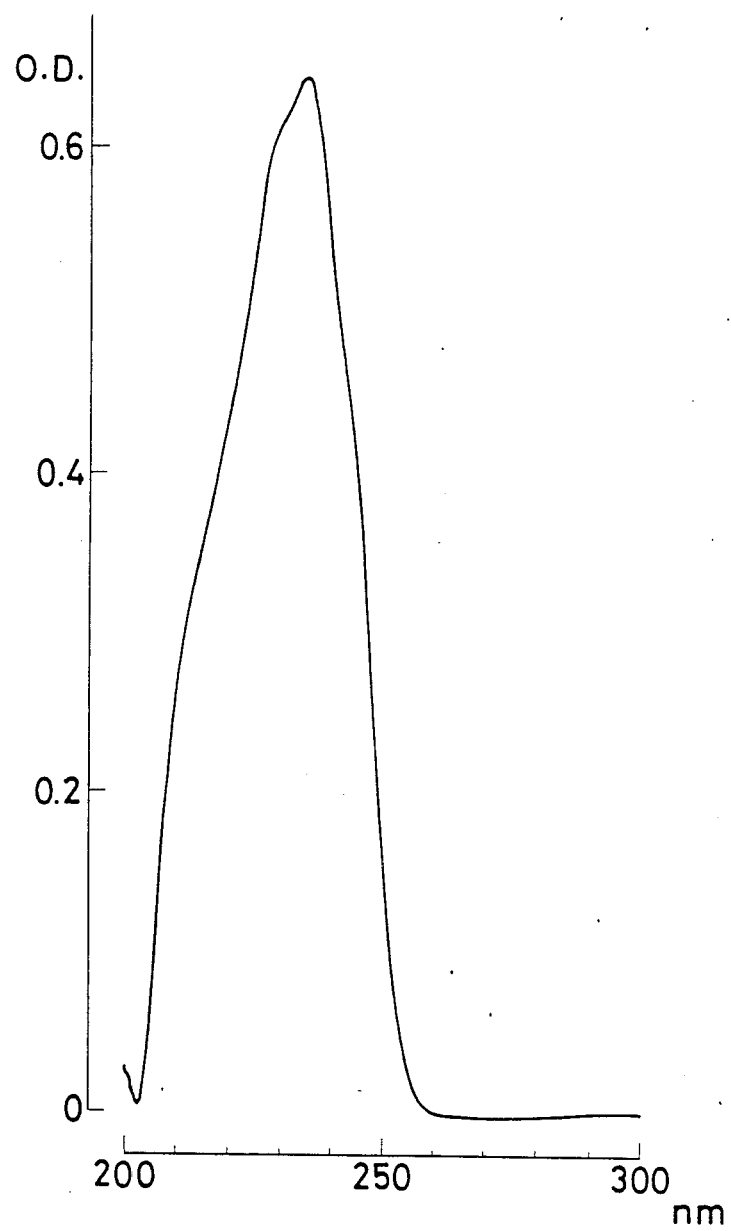
FIG. 1 is the ultraviolet absorption spectrum of antibiotic 82-85-8A.

(5) Ultraviolet absorption spectrum: shown in FIG. 1
Maximum absorption in methanol: 226 nm (shoulder), 231 nm, 240 nm (shoulder)

Figure 2:
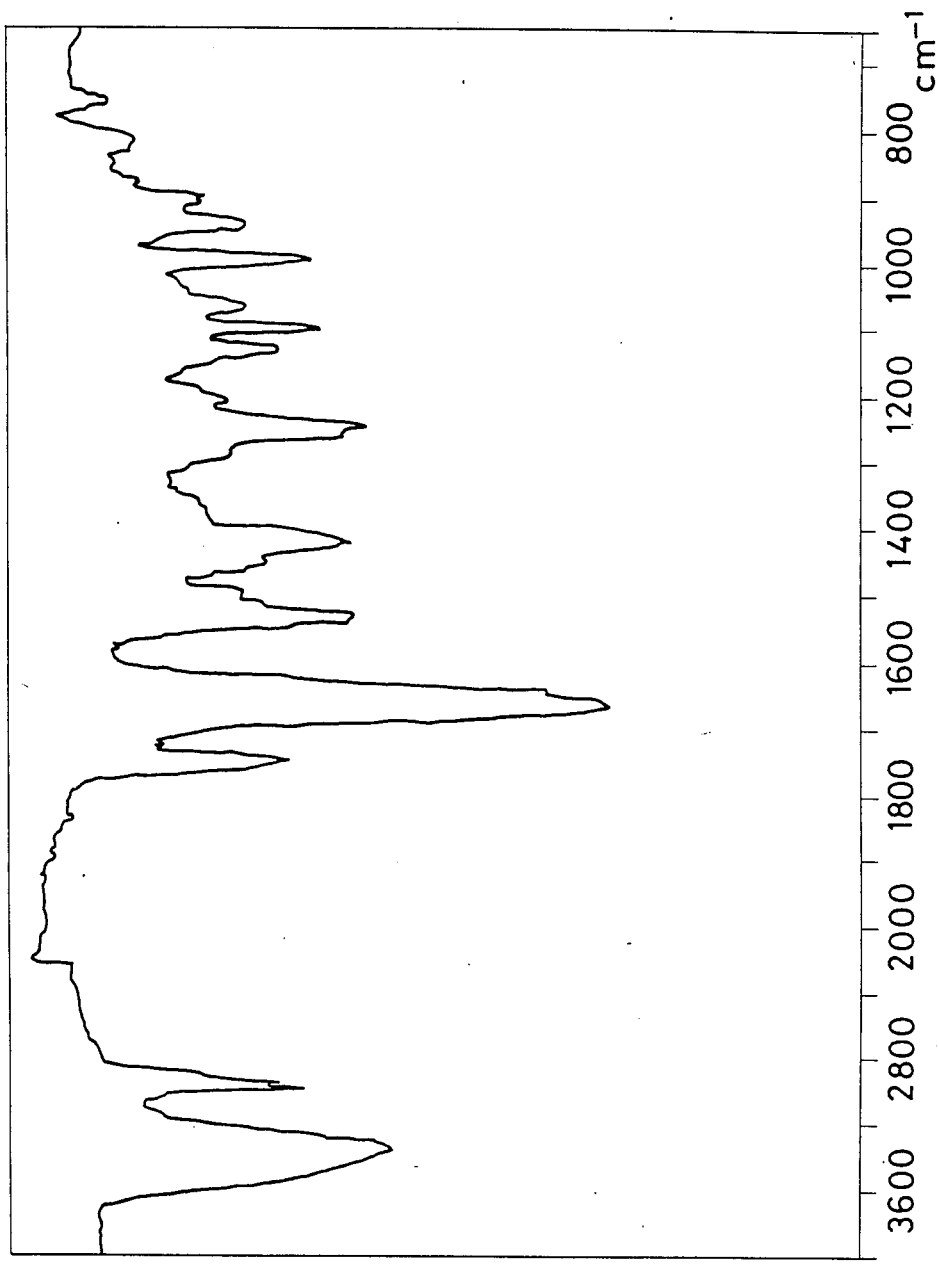
FIG. 2 is the infrared absorption spectrum of antibiotic 82-85-8A.

(6) Infrared absorption spectrum (KBr disc): shown in FIG. 2: 3340, 1664, 1640, 1530, 1422, 1260, 1244, 1125, 1100, 1067, 992 $cm^{-1}$ (7) Solubility:
Soluble: chloroform, dichloromethane, ethyl acetate, methanol, ethanol;
Slightly soluble: acetone;
Insoluble: hexane, water.

(8) Color reaction:
Positive: iodine, sulfuric acid, Dragendorf reaction
Negative: ninhydrin, ferric chloride (9) Nature: weakly basic substance

Figure 3:
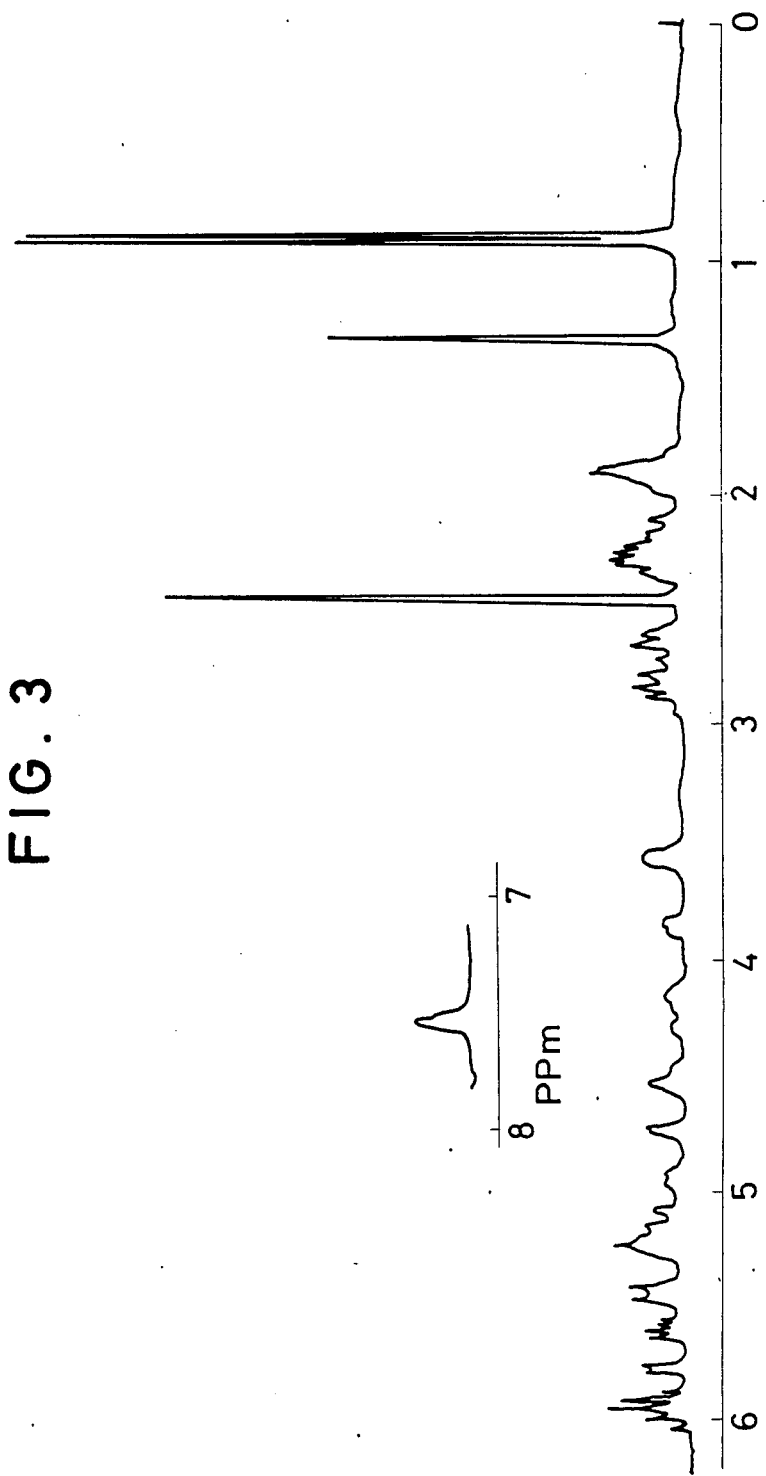
FIG. 3 is the proton nuclear magnetic resonance (NMR) spectrum of antibiotic 82-85-8A.

(10) H-NMR spectrum (in $CDCl_3$, inner standard; trimethylsilane (TMS), $\delta_{ppm}$): shown in FIG. 3

(11) Mass spectrum: main mass fragment peaks (EI-MS method): m/z; 726, 696, 617, 580, 503, 429, 355, 296, 259, 203, 187, 167, 150, 148, 128, 121, 110

(12) Rf-value; silica-gel TLC:

| Develop. solvent: | Rf-value: |
|---|---|
| chloroform-methanol (19:1) | 0.48 |
| chloroform-acetonitrile (17:3) | 0.07 |
| (Merck, Kieselgel 60 $F_{254}$ TLC plate) | |

(13) Stability: stable under acidic conditions at ambient temperature; slightly unstable under alkaline conditions over pH 10

As illustrated by the physico-chemical properties hereinabove, antibiotic 82-85-8A is a water-insoluble weakly basic peptidelactone antibiotic containing chlorine in its molecule.

Among prior known antibiotics resembling the present compound, monamycins, namely monamycin-$G_1$, -$G_2$, -$G_3$, -$H_1$, -$H_2$ and -I are known. Comparing both antibiotics, antibiotic 82-85-8A has different properties of molecular composition, molecular formula and nuclear magnetic resonance spectrum, and hence antibiotic 82-85-8A is confirmed as a novel antibiotic.

|  | Molecular Formula | M.W. |
| --- | --- | --- |
| Monamycin $G_1$ | $C_{34}H_{54}N_7O_8Cl$ | 723.5 |
| Monamycin $G_2$ | $C_{33}H_{54}N_7O_8Cl$ | 711.5 |
| Monamycin $G_3$ | $C_{33}H_{54}N_7O_8Cl$ | 711.5 |
| Monamycin $H_1$ | $C_{34}H_{56}N_7O_8Cl$ | 725.5 |
| Monamycin $H_2$ | $C_{34}H_{56}N_7O_8Cl$ | 725.5 |
| Monamycin I | $C_{35}H_{58}N_7O_8Cl$ | 739.5 |

The biological properties of antibiotic 82-85-8A are illustrated as follows:

(1) Antibacterial and antifungal activities:

Results of the paper disc method (Toyo filter paper, diameter 6 mm) are shown in Table 1.

TABLE 1

| Minimum Inhibitory Concentration (mcg/ml) | |
| --- | --- |
| Bacillus subtilis PCI 219 | 0.3 |
| Bacillus cereus | 0.6 |
| Micrococcus luteus ATCC 9341 | 0.3 |
| Staphylococcus aureus FDA 209P | 0.3 |
| Salmonella typhimurium | >100 |
| Shigella flexneri | >100 |
| Shigella sonnei E-33 | >100 |
| Escherichia coli NIHJ | >100 |
| Klebsiella pneumoniae PCI 602 | >100 |
| Aerobacter aerogenes | >100 |
| Proteus burugaris | >100 |
| Candida albicans KF 1 | >100 |
| Saccharomyces sake KF 26 | >100 |
| Schizosaccharomyces pombe IAM 4863 | >100 |
| Rhizopus japanicus IAM 6241 | >100 |
| Aspergillus nigar ATCC 6275 | >100 |
| Alternaria kikuchiana KF 185 | >100 |
| Mucor racemosus IFO 5403 | >100 |

As illustrated above, antibiotic 82-85-8A has strong antibacterial activities against Gram positive bacteria.

(2) Cell-cidal activity on HeLa $S_3$ cells:

The 50% cell-cidal value on HeLa $S_3$ cells is approximately 0.2 μg/ml. HeLa $S_3$ cells ($4 \times 10^4$ cells) were cultured in a medium for 2 days, and antibiotic 82-85-8A was added therein. After a further 3 days cultivation, the cells were counted.

(3) Toxicity:

$LD_{50}$, mice, intraperitoneal administration: Approximately 3.8 mg/kg

Antibiotic 82-85-8A and its acid addition salts having antibacterial activity and cell-cidal activity, are expected to be useful as a medicament antibiotic, especially for treatment of Gram-positive bacterial infections or as an antitumor agent.

The following examples illustrate the present invention but are not to be construed as limiting.

EXAMPLE 1

Fermentation

Streptomyces sp. No. 82085 FERM-P No. 8140, cultured on an agar slant medium containing glucose 1.0%, peptone 0.5%, meat extract 0.5%, NaCl 0.3% and agar 1.2%, at 27° C. for 14 days, was inoculated in a sterilized liquid medium (100 ml, pH 7.0) containing glucose 2.0%, peptone 0.5%, meat extract 0.3%, dry yeast 0.3% NaCl 0.5% and calcium carbonate 0.3% (A-medium) and reciprocally shake cultured (stroke 17 cm, frequency 120 min.) at 27° C. for 72 hours to prepare a seed culture.

In a 600 lit. tank, A-medium (300 lit.) was prepared, sterilized, aseptically inoculated with the seed culture obtained hereinabove and submerged aeration cultured at 27° C., with aeration of 150 lit./min. for 3 days with agitating to obtain a cultured broth (290 lit.)

EXAMPLE 2

Extraction of Antibiotic

Cultured filtrate obtained in Example 1 was mixed with Hyfrosuper-cell (trade name) (15 kg) and filtered to obtain a filtrate (260 lit.) which was adjusted to pH 6 by adding 6N HCl. Ethyl acetate (150 lit.) was mixed with the filtrate, the mixture was stirred and the antibiotic 82-85-8A was extracted. The aqueous layer was again mixed with ethyl acetate (150 lit.) and stirred. The combined ethyl acetate layer was concentrated in vacuo to approximately 10 lit., then washed with de-ionized water (5 lit.) The organic layer was dehydrated by adding anhydrous sodium sulfate, and was distilled in vacuo to obtain as an oily brownish substance antibiotic 82-85-8A.

EXAMPLE 3

Silica-gel Chromatography of Antibiotic

The oily substance obtained in Example 2 was charged on a column (95×500 nm) of silica gel 60 (Merck), which was previously packed with chloroform, and chromatographed by continuous exchanging the elution solvent from chloroform to methanol. The eluted fractions showing antibacterial activity against Micrococcus luteus ATCC 9341 were collected, and concentrated in vacuo to obtain antibiotic 82-85-8A with approximately 50% purity.

EXAMPLE 4

Isolation of Antibiotic by HPLC

The purification of the crude antibiotic 82-85-8A obtained in Example 3 was performed by means of high speed liquid chromatography apparatus, assembled from the following parts.

Injection pump: TRIROTAR-V (Japan Spectrometry Corp.);

Detector: UVIDEC-100-V (Japan Spectrometry Corp.);

Column: Octadecyl silylated silica gel in YMC packed column A-324, inner diameter 10 mm×length 300 mm. (Yamamura Chem. Inst. Inc.).

Crude antibiotic 82-85-8A (5 mg) dissolved in methanol (300 μl) was injected and eluted with a mixture of water-methanol (3:7). The fraction showing peak absorption at 232 nm was collected and concentrated in vacuo to obtain purified antibiotic 82-85-8A.

EXAMPLE 5

Isolation of Antibiotic by Preparative TLC

Silica gel 60 $F_{254}$, 20×20 cm (Merck) was used for preparative thin layer chromatography. Partially purified antibiotic 82-85-8A (20 mg) dissolved in a small amount of chloroform was spotted on a streak line. The plate was developed with a mixed solvent of chloroform-methanol (19:1). Antibiotic 82-85-8A was checked by irradiating with an ultraviolet lamp and the band showing antibiotic 82-85-8A was scratched off which was extracted with chloroform to obtain purified antibiotic 82-85-8A (10 mg).

What is claimed is:

1. A member selected from the group consisting of antibiotic 82-85-8A of the following physico-chemical properties:
    (1) Elementary analysis: $C_{31}H_{47}N_8O_{10}Cl$ (determined by high resolution mass spectrometry)
    (2) Molecular weight: 726.5 (determined by field desorption mass spectrometry and calculated from elementary analysis)
    (3) Melting point: 162°–167° C. (partially immersed at 160° C., completely melted at 167° C., no browning)
    (4) Specific rotation: $[\alpha]_D^{20} = -56°$ (c=0.24, methanol)
    (5) Ultraviolet absorption spectrum (in methanol): shown in FIG. 1
    (6) Infrared absorption spectrum (KBr): shown in FIG. 2
    (7) Solubility:
        soluble: chloroform, dichloromethane, ethyl acetate, methanol, ethanol,
        slightly soluble: acetone,
        insoluble: hexane, water;
    (8) Color reaction:
        Positive: iodine, sulfuric acid, Dragendorf reaction
        Negative: ninhydrin, ferric chloride
    (9) Nature: weakly basic substance,
and a pharmacologically acceptable non-toxic salt thereof.

2. A process for the production of antibiotic 82-85-8A which comprises culturing an antibiotic-82-85-8A-producing microorganism Streptomyces sp. No. 82-85, FERM-P No. 8140 in a culture medium until substantial antibiotic activity is imparted to said medium, and isolating the thus-produced antibiotic 82-85-8A from the cultured medium.

3. A process according to claim 2, and converting the thus-produced antibiotic to a pharmacologically acceptable non-toxic salt thereof.

* * * * *